United States Patent
Causevic (10) Patent No.: US 8,700,141 B2
(45) Date of Patent: Apr. 15, 2014

(54) METHOD AND APPARATUS FOR AUTOMATIC EVOKED POTENTIALS ASSESSMENT

(75) Inventor: Elvir Causevic, Clayton, MO (US)

(73) Assignee: Brainscope Company, Inc., Bethesda, MD (US)

(*) Notice: Subject to any disclaimer, the term of this patent is extended or adjusted under 35 U.S.C. 154(b) by 262 days.

(21) Appl. No.: 12/720,907

(22) Filed: Mar. 10, 2010

(65) Prior Publication Data

US 2011/0224570 A1 Sep. 15, 2011

(51) Int. Cl.
*A61B 5/04* (2006.01)

(52) U.S. Cl.
USPC .......................................... 600/544

(58) Field of Classification Search
USPC ................................. 600/544, 545
See application file for complete search history.

(56) References Cited

U.S. PATENT DOCUMENTS

| | | | |
|---|---|---|---|
| 4,279,258 A | 7/1981 | John | |
| 4,564,022 A | 1/1986 | Rosenfeld et al. | |
| 4,736,751 A * | 4/1988 | Gevins et al. | 600/545 |
| 5,447,166 A * | 9/1995 | Gevins | 600/544 |
| 5,467,777 A | 11/1995 | Farwell | |
| 5,611,350 A * | 3/1997 | John | 600/378 |
| 6,067,467 A | 5/2000 | John | |
| 6,317,627 B1 * | 11/2001 | Ennen et al. | 600/544 |
| 6,589,189 B2 | 7/2003 | Meyerson et al. | |
| 2004/0010203 A1 | 1/2004 | Bibian et al. | |
| 2004/0077967 A1 * | 4/2004 | Jordan | 600/544 |
| 2005/0177058 A1 * | 8/2005 | Sobell | 600/545 |
| 2007/0032737 A1 * | 2/2007 | Causevic et al. | 600/544 |
| 2007/0106169 A1 | 5/2007 | Fadem | |
| 2007/0255164 A1 | 11/2007 | Viertio-oJa et al. | |
| 2007/0299359 A1 | 12/2007 | Olsson et al. | |
| 2008/0208073 A1 | 8/2008 | Causevic | |
| 2009/0062676 A1 * | 3/2009 | Kruglikov et al. | 600/544 |
| 2010/0041962 A1 | 2/2010 | Causevic et al. | |
| 2011/0144520 A1 * | 6/2011 | Causevic et al. | 600/544 |
| 2011/0182143 A1 * | 7/2011 | Liu et al. | 367/47 |

OTHER PUBLICATIONS

Anderer et al., "Artifact Processing in Computerized Analysis of Sleep EEG—A Review," Neuropsychobiology, vol. 40, pp. 150-157, 1999.
Claassen et al., "Continuous Electroencephalographic Monitoring in Neurocritical Care," Current Neurology and Neuroscience Reports, vol. 2, pp. 534-540, 2002.
Durka et al., "A Simple System for Detection of EEG Artifacts in Polysomnographic Recordings," IEEE Transactions on Biomedical Engineering, vol. 50, No. 4, pp. 526-528, Apr. 2003.
Gevins et al., "Normative Data Banks and Neurometrics. Basic Concepts, Methods and Results of Norm Constructions," Handbook of Electroencephalography and Clinical Neurophysiology (Revised Series vol. 1), pp. 449-495, 1987.
Guerit, "Medical technology assessment EEG and evoked potentials in the intensive care unit," Neurophysiol Clin., vol. 29, pp. 301-317, 1999.
Hall, "Intensive Care Unit (ICU) Monitoring," Handbook of Auditory Evoked Responses, pp. 534-579, 1992.

(Continued)

*Primary Examiner* — Navin Natnithithadha
*Assistant Examiner* — Etsub Berhanu
(74) *Attorney, Agent, or Firm* — Finnegan, Henderson, Farabow, Garrett & Dunner, LLP (57) ABSTRACT

Systems and methods for assessing a patient's neurologic state based on auditory evoked responses are provided.

30 Claims, 4 Drawing Sheets

(56) References Cited

OTHER PUBLICATIONS

Jacquin et al., "Automatic Identification of Spike-Wave Events and Non-Convulsive Seizures with a Reduced Set of Electrodes," Proceedings of the 29th Annual International Conference of the IEEE EMBS, pp. 1928-1932, Aug. 2007.

John et al., "Neurometric Classification of Patients with Different Psychiatric Disorders," In Statistics and Topography in Quantitative EEG, Ed., D. Sampson-Dollfus, pp. 88-95, Paris: Elsevier, 1988.

Jung et al., "Removing electroencephalographic artifacts by blind source separation," Psychophysiology, vol. 37, pp. 163-178, 2000.

Lehnertz et al., "Can Epileptic Seizures be Predicted? Evidence form Nonlinear Time Series Analysis of Brain Electrical Activity," Physical Review Letters, vol. 80, No. 22 pp. 5019-5022, 1998.

MacCrimmon et al., "Computerized Pattern Recognition of EEG Artifact," Brain Topography, vol. 6, No. 1, pp. 21-25, 1993.

Romero et al., "A comparative study of automatic techniques for ocular artifact reduction in spontaneous EEG signals based on clinical target variables: A simulation case," Computers in Biology and Medicine 38, pp. 348-360, 2008.

Thatcher et al., "An EEG Severity Index of Traumatic Brain Injury," J. Neuropsychiatry Clin Neurosci, vol. 13, No. 1, pp. 77-87, 2001.

U.S. Appl. No. 12/702,861, filed Mar. 10, 2010.

Vespa et al., "Early detection of vasospasm after acute subarachnoid hemorrhage using continuous EEG ICU monitoring," Electroencephalography and clinical Neurophysiology, vol. 103, pp. 607-615, 1997.

Causevic et al., "Fast Wavelet Estimation of Weak Biosignals," Engineering, IEEE Service Center, Piscataway, NJ, vol. 52, No. 6, pp. 1021-1032, 2005.

Jacquin et al., "Adaptive complex wavelet-based filtering of EEG for extraction of evoked potential responses", Proc. IEEE Int. Conf. Acoust., Speech, and Signal Proc., Philadelphia, PA, Mar. 2005, pp. V:393-396.

Jacquin et al., "Optimal denoising of Brainstem Auditory Evoked Response (BAER) for automatic Peak Identification and Brainstem Assessment", Proceedings of the 28th IEEE EMBS Annual Int'l Conference, New York, Aug. 30-Sep. 3, 2006, pp. 1723-1726.

PCT International Search Report and Written Opinion issued on Jun. 17, 2011 in PCT/US2011/027651.

PCT International Search Report and Written Opinion mailed Jul. 4, 2011, in related PCT/US2011/027525.

* cited by examiner

METHOD AND APPARATUS FOR AUTOMATIC EVOKED POTENTIALS ASSESSMENT

The present disclosure pertains to devices and methods for monitoring changes in a neurologic state of a patient, and more particularly, to systems and methods for monitoring auditory evoked response.

There are numerous surgical and medical conditions that can cause potentially deleterious changes in brain or brain stem function. For example, moderate or severe central nervous system injury can results from trauma (e.g., due to an impact or other injury to the head), metabolic disorders, infections, expanding intracranial masses, intracranial hemorrhage, illicit or prescription drug use, and iatrogenic sources (e.g., post-operatively or as a medical treatment side effect). Whatever the cause, it would be desirable to have better noninvasive methods for evaluating head injury and, when needed, providing appropriate medical or surgical interventions before potentially serious or irreversible neurological damage occurs. In addition, portable neurologic monitors that allow assessment of head injuries at more remote locations (e.g., on the battlefield or at accident sites) may allow more appropriate patient assessment and treatment.

In the clinical setting, changes in neurologic state may be suspected based on declining mental status, abnormal neurological signs, and other physical findings, such as changes in the appearance of the optic nerve when viewed through an opthalmoscope. However, monitoring neurologic status through these methods presents a number of challenges. For example, many surgical patients or seriously ill medical patients will be sedated or unconscious, thereby making it impossible to evaluate certain changes in mental status. In addition, changes in physical exam findings, such as a change in the optic nerve, may be discovered after significant neurologic damage has occurred, thereby preventing timely intervention. In addition, implantable monitors are less desirable since they require an invasive procedure and impart other potential risks (e.g., infection).

The systems and methods of the present disclosure to provide easy-to-use tools for assessing and monitoring head injuries.

SUMMARY

A system for monitoring brain electrical activity is provided. The system comprises a set of electrodes, at least one auditory stimulus generator, and a detection system operatively connected to the set of electrodes and configured to receive electrical signals detected by the electrodes after production of an auditory stimulus by the stimulus generator, the electrical signals representing an auditory evoked response. The system further comprises a processor circuit including electrical circuitry configured to perform the steps of: removing artifact noise from the signal; performing a non-linear denoising step on the signal; performing a non-linear transform on the signal; producing a set of non-linear features related to the patient's auditory brain stem response; and comparing the set of non-linear features to one or more feature sets stored in a storage system and determining if the non-linear features are indicative of an abnormal neurologic state.

A method for monitoring brain electrical activity is provided. The method comprises applying a set of electrodes to a patient, generating at least one auditory stimulus that can be detected by the patient, and recording an electrical signal detected by the electrodes after production of an auditory stimulus by the stimulus generator, the electrical signal representing an auditory evoked response; removing artifact noise from the signal. The method further comprises performing a non-linear denoising step on the signal; performing a non-linear transform on the signal; producing a set of non-linear features of the signal; and comparing the set of non-linear features to one or more feature sets stored in a storage system and determining if the non-linear features are indicative of an abnormal neurologic state.

DESCRIPTION OF EXEMPLARY EMBODIMENTS

The present disclosure provides a system and method for monitoring brain electrical activity, including assessment of auditory brainstem responses (ABR) to assess neurologic function. In certain embodiments, the system and method allow rapid, automatic, and/or continuous monitoring of ABR signals, or other evoked potential signals. The system and method can assist in determining the severity of certain injuries due, for example, to trauma, infection, medical disorders (e.g., inflammatory disorders, adverse drug reactions), and/or post-surgical complications. In certain embodiments, the systems and methods allow rapid assessment of the severity and/or progression of problems due to traumatic brain injury due, for example to an impact to the head. In certain embodiments, the systems and methods allow continuous, non-invasive monitoring of intracranial pressure (ICP).

As described further below, the system includes a set of electrodes and an auditory stimulus for generating and detecting ABR and other auditory evoked potential signals from a patient. The system and method further include processes for automatically removing raw artifact noise from the signal and performing a non-linear denoising step on the signal to generate a sufficiently high signal-to-noise ratio to allow automatic ABR evaluation. The system and method can further include non-linear processing techniques including, for example, performing a non-linear transform on the signal and producing a set of non-linear features related to the patient's auditory brain stem response. These non-linear features can be compared to one or more feature sets stored in a storage system to determine if the non-linear features are indicative of an abnormal neurologic state.

Figure 1A:
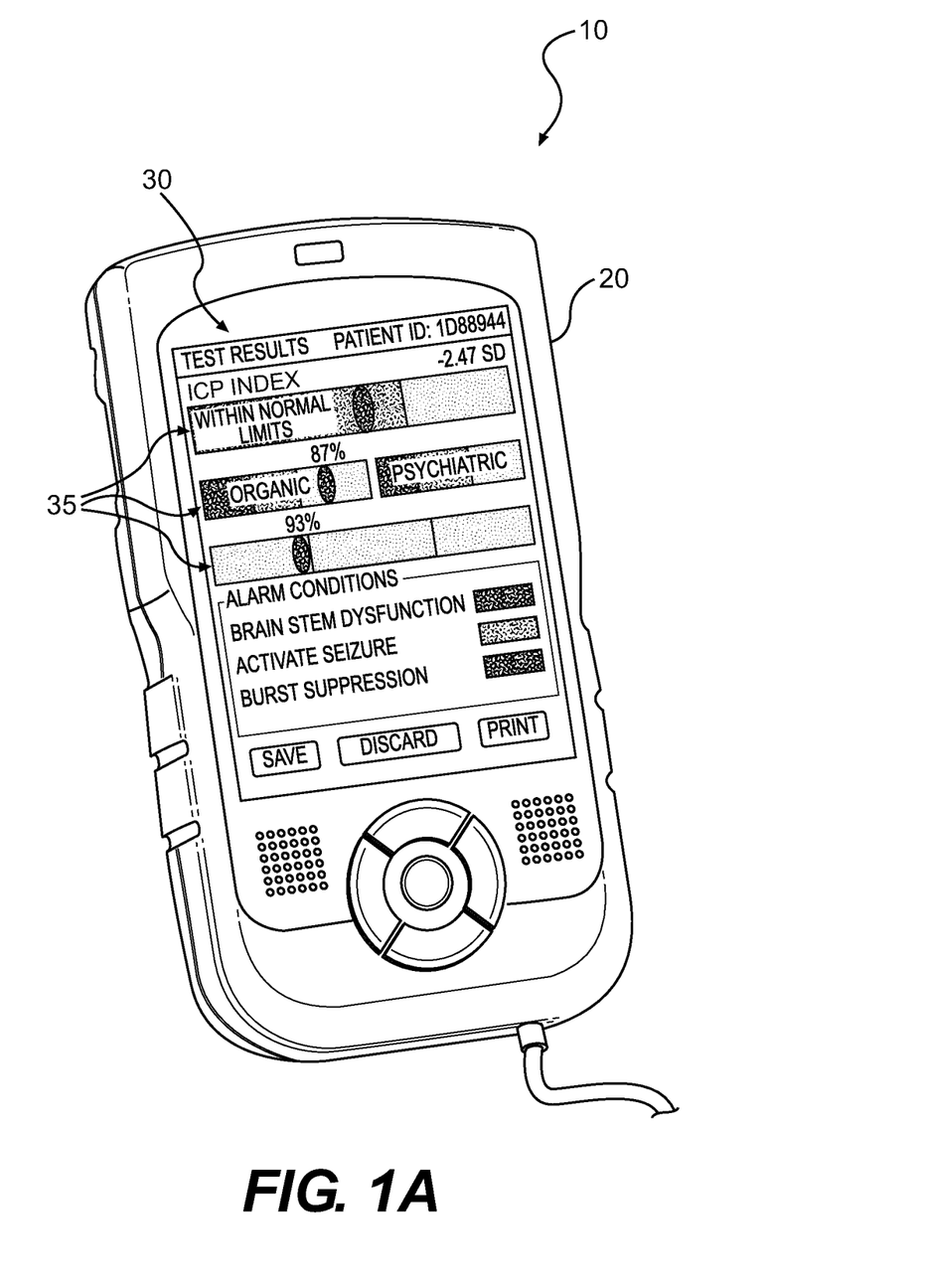
FIG. 1A illustrates a brain electrical activity monitoring system according to one embodiment of the present disclosure.

FIG. 1A illustrates a brain electrical activity monitoring system 10, according to certain embodiments of the present disclosure. As shown, the brain electrical activity monitoring system 10 can include an enclosure 20 containing electrical circuitry configured to perform data processing, stimulus generation, and analysis for diagnosis and patient monitoring. In addition, the enclosure 20 may further include a display system 30, such as an LCD or other visual display to provide real-time, easy-to-interpret information related to a patient's clinical status.

In some embodiments, the brain electrical activity monitoring system 10 will include circuitry configured to provide real-time monitoring of brain electrical activity. The system 10 will provide rapid data acquisition, processing, and analysis to allow point-of-care diagnosis and assessment. For example, as shown, the display system 30 can include one or more indicators 35, or visual displays, that are configured to display an easy-to-interpret indication of a patient's status. In one embodiment, the indicators 35 will include an indication of where a patient's status lies relative to a normal data set, a patient's status relative to a base line, and/or one or more indicators of the origin of any abnormalities. In some embodiments, the indicators provide a scale (from normal to severely abnormal). Accordingly, the scale provides an indication of the severity of an injury, elevation in ICP, or abnormality in brain stem function.

In addition, the brain electrical activity monitoring system 10 may include one or more alert systems for notifying a caregiver of an abnormality or changing condition. In some embodiments, the system further includes a communication device configured to automatically generate a signal representing the patient's neurologic state. Such communication devices can include visual display systems and/or audible alerts that may be easily understood by patient care givers. In addition, in some embodiments, the alert systems can be remote from the monitoring system, to allow remote monitoring and intervention by health care personnel.

In certain embodiments, the visual display indicates a deviation from a baseline measurement, as described further below. In addition, the system can include at least one second visual display indicating at least one diagnostic state. For example, the diagnostic state can indicate, elevated intracranial pressure, cerebral edema, compromised brainstem function, or dysfunction of higher parts of the neural auditory pathway, including the cognitive function relating to auditory stimulus perception. In some embodiments, the communication system includes a visual display indicating a deviation from a baseline measurement indicative of ICP for a patient.

Figure 1B:
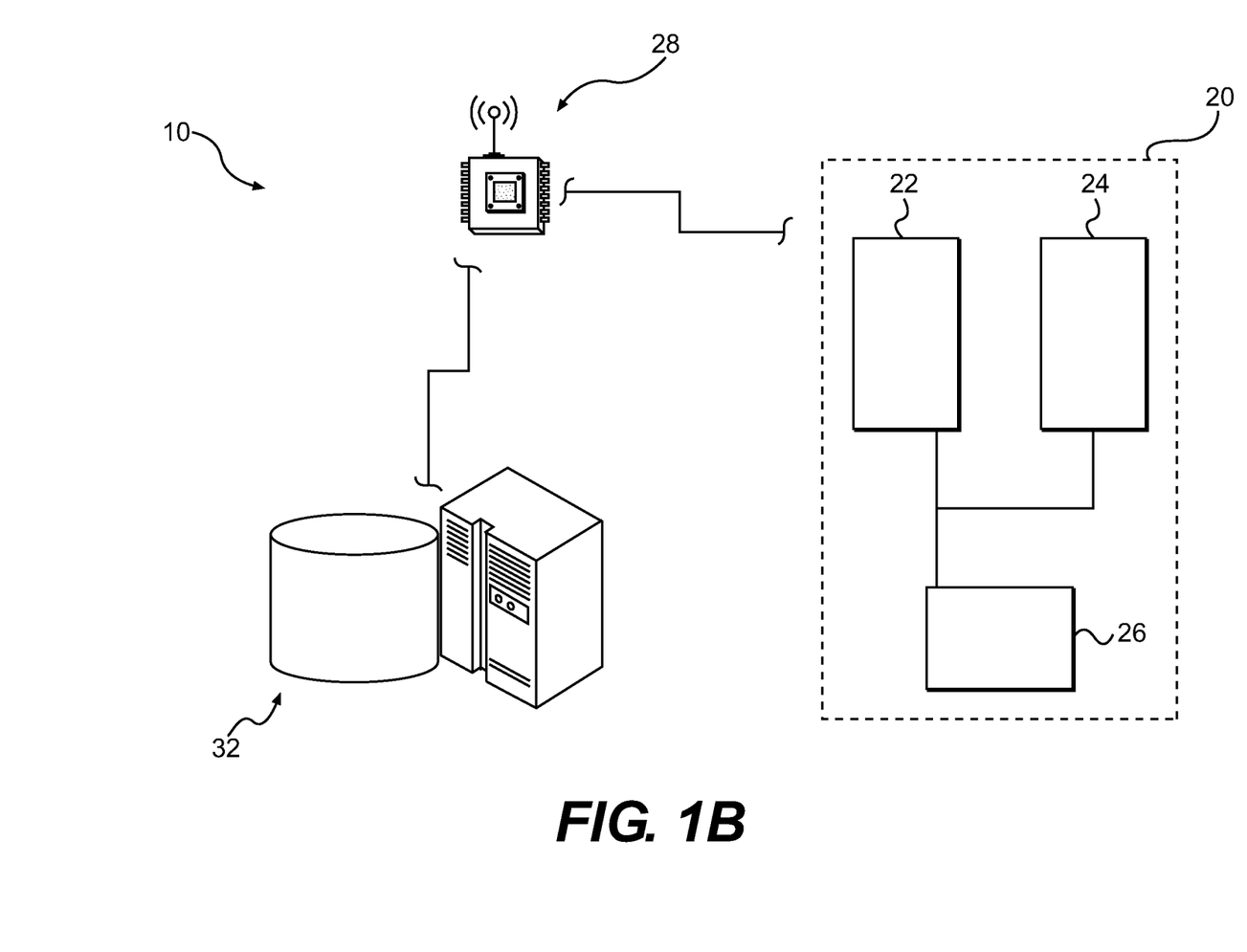
FIG. 1B illustrates a schematic diagram of the monitoring system of FIG. 1A, illustrating additional components.

FIG. 1B illustrates a schematic diagram of the monitoring system of FIG. 1A, illustrating additional components. As shown, the enclosure 20, can include a number of component parts. For example, the enclosure 20 may include a memory unit or storage system 22 configured to store data related to patient brain electrical activity data measurements, or a database of normal and/or pathological readings. Further, the enclosure will include circuitry configured to process and evaluate electrical signals and data 24, and a transmitter unit 26.

Figure 2A:
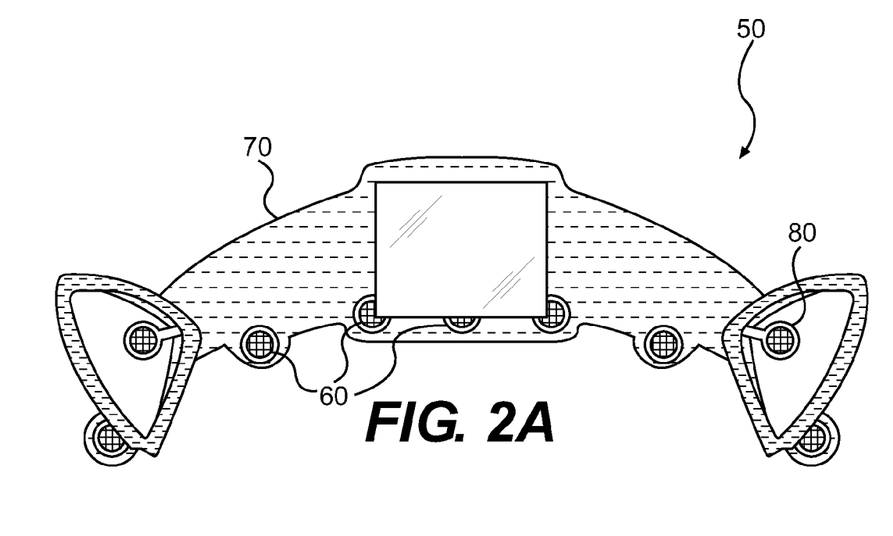
FIG. 2A illustrates an electrode set for use with the brain electrical activity monitoring system of the present disclosure.
Figure 2B:
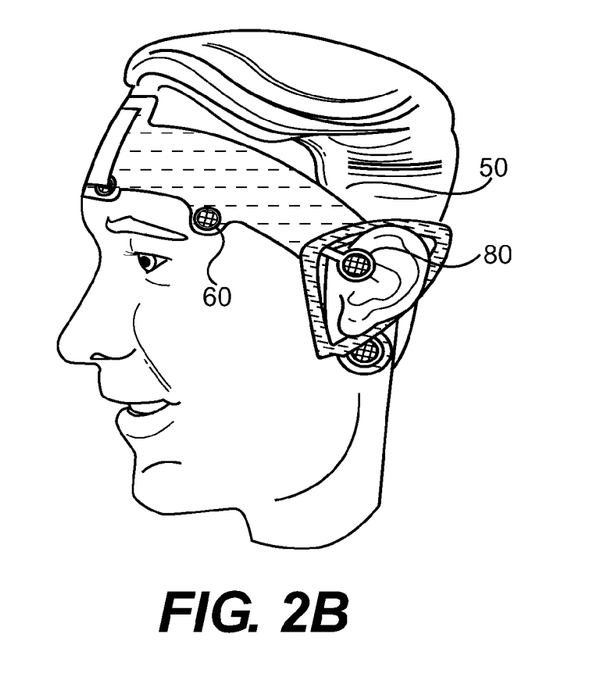
FIG. 2B illustrates the electrode set of FIG. 1B, as applied to a patient.

The circuitry 24 can include a number of circuitry types. For example the circuitry 24 can include processing circuitry configured to receive electrical signals from electrodes, as shown in FIGS. 2A-2B, and to convert such signals into data that can be further evaluated. In some embodiments, the circuitry can be configured to enable nonlinear processing, including nonlinear amplifiers. Further, the circuitry 24 can also include components configured to allow analysis of processed data and comparison of brain electrical activity data to normal data, or to previous or future measurements, as described in more detail below. Further, it will be understood that, although shown as a single component, multiple components can be included, either on a single chip or multiple chips.

The transmitter unit 26 can include a number of transmitter types. For example, the transmitter 26 may include a hardware connection for a cable or a telemetry system configured to transmit data to a more distant receiver 28, or a more powerful transmission system to redirect data to a database 32 that may be stored nearby or at a remote or distant location. In certain embodiments, the data can be transmitted and stored and/or evaluated at a location other than where it is collected.

The brain electrical monitoring system 10 may be configured to attach to various patient interfaces. For example, FIGS. 2A-2B illustrate an electrode set 50 for use with the brain electrical activity monitoring system 10 of the present disclosure. As shown, the electrode set 50 includes one or more electrodes 60 for placement along the patient's forehead and mastoid region. As shown, the electrode set 50 includes a limited number of electrodes 60 to facilitate rapid and easily repeated placement of the electrodes 60 for efficient, but accurate, patient monitoring. Further, in one embodiment, the electrodes 60 may be positioned on a head band 70 that is configured for easy and/or rapid placement on a patient, as shown in FIG. 2B. Further, it will be understood that other electrode configurations may be selected, which may include fewer or more electrodes.

As noted, the electrode set 50 will be operably connected to the monitoring system 10. Generally, the electrodes 60 will be electrically coupled with the monitoring system 10 to allow signals received from the electrodes to be transmitted to the monitoring system 10. Such an electrical coupling will generally be through one or more electrical wires, but nonphysical connections may also be used.

Further, as shown, a signal production device 80 may be provide, and may be attached to the head band 70 or contained separately. As shown, the device 80 includes an auditory stimulus generator configured to produce audible signals to facilitate measurement of brain electrical activity in response to auditory stimuli. Further, the monitoring system 10 may also include other stimulation generating systems such as visual, tactile, taste, and olfactory stimulation systems. Further, the stimulation devices may be attached to the electrode set 50 or may be contained in separate components.

In some embodiments, the electrode set 50 will include electrodes positioned to allow detection of various types of brain electrical activity. For example, various forehead or scalp electrodes may be included to allow detection of cortical activity, or to assist in identification of signal artifacts to be removed during raw denoising. Further, other electrodes may be positioned to allow detection of brain stem functions (e.g., mastoid or occipital electrodes). In some embodiments, the electrode set is positioned on a head band and includes at least two electrodes positioned on the head band to allow detection of auditory evoked response signals when the headband is positioned on a patient.

Figure 3:
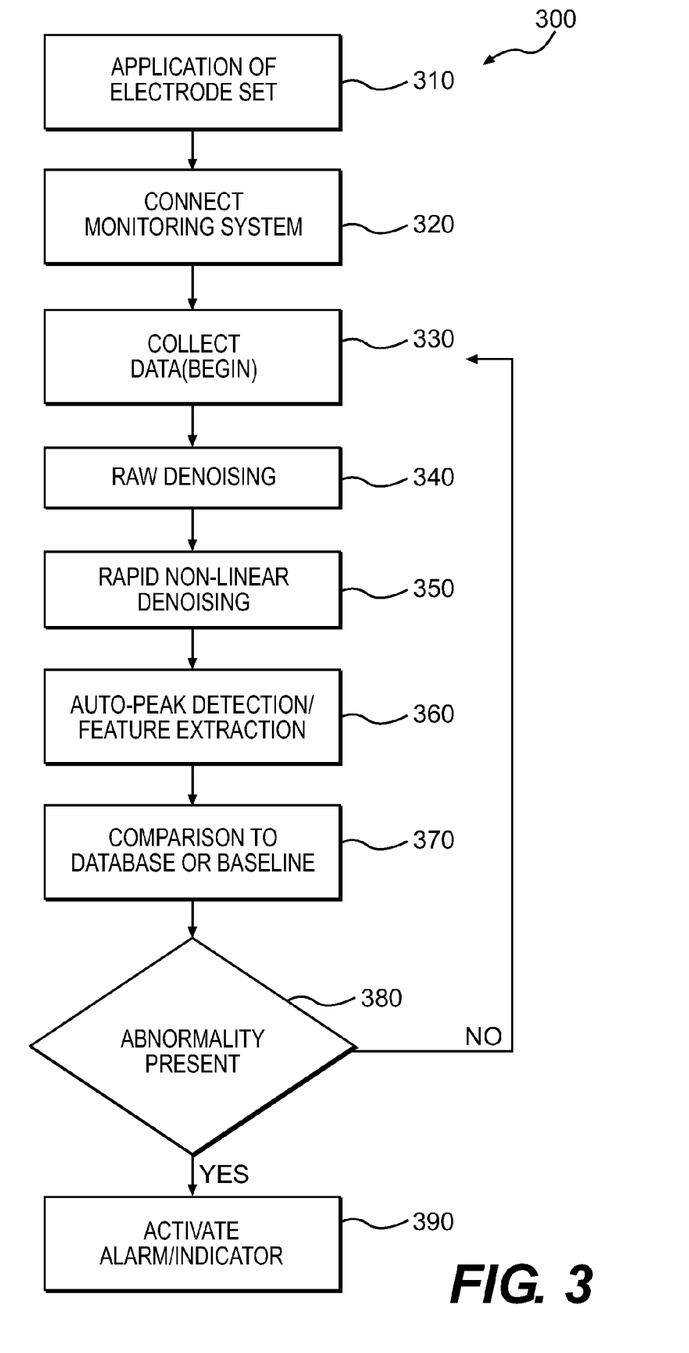
FIG. 3 illustrates a method for automatically processing a signal to assess a neurologic state of a patient, according to certain embodiments.

FIG. 3 illustrates a method for automatically processing a signal to assess a neurologic state of a patient, according to certain embodiments. As shown, the process includes application of an electrode set to a patient's head, as shown at Step 310. Next, the brain activity monitoring system is connected to the electrode set, as shown at Step 320, and data collection is begun, as shown at Step 330. As noted above, the data collection can include measurement and recording of ABR signals after generation of audible stimuli produced by a stimulus generator.

After collection of ABR or other evoked auditory response signal data, the data can be processed to allow automatic neurologic assessment and monitoring. Accordingly, raw denoising is first performed, as shown at Step 340 to reduce signal artifacts. The raw denoising can be performed using an automated process that does not require a trained technician, as described in more detail below.

After raw denoising, a rapid non-linear denoising process is used to produce a suitable signal-to-noise ratio. In certain embodiments, a wavelet denoising algorithm is used. For example, a suitable denoising algorithm include Cyclic Shift Tree Denoising (CTSD), which is described by Causevic et al. in "Fast Wavelet Estimation of Weak Biosignals," Biomedical Engineering, Vol. 52(6): 1021-32, 2005. In certain embodiments, to facilitate automatic, real-time monitoring, a CTSD process may be performed real time, such that incoming data is buffered and the algorithm is completed on the buffered date. In addition, as new data is received (i.e., a new data frame comes in), the new data can be is added to the buffer on a first in/first out basis, and the algorithm is repeated.

In some embodiments, the CTSD method is adapted for continuous measurement, such that new frames are adapted into the algorithm in real time in batches. For example, a time at which the CTSD is performed can be set, and as each level of CTSD progresses, a new epoch of fresh ABR data is inserted into the process in parallel. In certain embodiments, a linear averaging process can be employed to arrive at an averaged waveform, synchronized to the auditory stimulus. This result can be combined with the CTSD result, sample by sample, or averaged.

After denoising, the signal can be further processed to identify certain non-linear features, as shown at step 360. In certain embodiments, a non-linear transform is performed followed by a process for detecting the location of ABR peaks in the non-linear domain. In addition, various other non-linear features can be identified and stored for comparison to patient baseline, normative, or population data, as described further below.

In various embodiments, automatic peak detection can be performed by using a set of non-linear methodologies, such as a non-linear transform (e.g., a wavelet transform), while keeping the CTSD coefficients in the non-linear/wavelet domain and searching for local peaks in that domain independently. The peaks information in the non-linear domain is then combined with the time domain peak detection methods in a single classifier, or a using a voting classifier scheme.

In addition, various other non-linear features can be extracted from the signal, such that in addition to the actual peak locations, other qualitative information about the peaks is calculated, including, for example, various local and global maxima of the non-linear features (including number and location, nth order moments, vanishing moments, area under the curve of non-linear coefficients, etc. In certain embodiments, linear features of the waveform can be extracted such as amplitude, power, phase, frequency spectrum, or others, and those features can be combined with non-linear features.

After peak detection and feature extraction are performed, the non-linear and/or linear features can be compared to data stored in a database and/or to prior data obtained from the same patient to allow assessment and monitoring of the patient's neurologic state, as shown at Step 380. In addition, if abnormalities are detected, an alarm or indicator can be active, as shown at step 390, or a normal condition can be indicated. Further, if no abnormality is detected, or if continued monitoring of an abnormal patient is needed, measurements can be repeated continuously or periodically, to allow ongoing patient monitoring. In some embodiments, this comparison may include a multivariate comparison.

In some embodiments, the database includes prior auditory evoked response measurements for the same patient, and the set of non-linear features are compared to one or more feature sets stored from the prior measurements and determine if any changes have occurred.

In various embodiments the database includes ABR or other evoked potential data from a group of other patients having an identified neurologic state. For example, the database can include a database of normal patients and patients with a variety of different abnormalities, including, for example, traumatic brain injury at various times after injury, infection, edema, elevated ICP. In some embodiments, the system includes a database of auditory evoked response data for a group of patients, and the patient's neurologic state is classified based on a similarity between one or more non-linear features of the patient's auditory evoked response and one or more non-linear features of at least one other patient having a known neurologic state.

A variety of non-linear features can be used to assess the patient's neurologic state. For example, the timing of ABR peaks has been shown to change due to trauma and/or increased intracranial pressure. However, automatic detection of ABR peaks is difficult, and therefore, automatic assessment of brain abnormalities has not been successful. The signal processing techniques of the present disclosure allow automatic peak detection and feature extraction in the non-linear domain, and therefore, facilitate automatic neurologic monitoring. Accordingly, in certain embodiments, the non-linear features set identified as described above, can include the location, amplitude or time of one or more peaks in an auditory evoked response.

As noted above, in various embodiments, the system and method of the present disclosure can provide an indication of an elevation in ICP. In some embodiments, the indication can be based on a sliding scale from normal to severely abnormal, without providing an absolute value of ICP. In this way, the system provides information of clinical significance, for example, warning of potential deleterious changes in brain stem function, as indicated by changes in ABR, without the need for an invasive ICP monitor. In other embodiments, a correlation between ICP and the ABR data is made to provide an estimation of ICP.

Example

Sample Algorithm

One typical specific algorithm for feature extraction and classification is described below. This algorithm may be used to identify abnormalities in ICP or assess the severity of a traumatic brain injury:

(1) Take CTSD averaged ABR waveform, with sufficiently high estimated SNR (e.g., Fsp>3.1), of length 15 ms, including saved wavelet coefficients (2) Calculate "string length" of the entire waveform and save.

(3) Calculate first half "string length" 0-7.5 ms and second half 7.5-15 ms, and save.

(4) Calculate a Pearson correlation coefficient (r) with a series of sinewaves of length 15 ms, starting from 1 Hz to 1000 Hz, save vector of top ten r's (highest correlation), and slide index (likely peak location).

(5) Produce wavelet coefficients using biorthogonal wavelets, save top 50% of coefficients by amplitude.

(6) Produce nearest-neighbor search for peak detection (edge detection/sign change), filter to find local maxima, save.

Put together all the features in a vector, multiplying each of the features with a pre-determined weight factor based on a training data set with manually pre-identified peaks and invasive ICP recordings, and then classify new signals.

Raw Denoising:

Most systems that rely on quantitative analysis of brain electrical activity typically assume that a trained technologist has manually edited the raw data to remove artifacts. However, the editing process can be time-consuming and is inherently subjective. In addition, the need for technologist editing prevents automated monitoring or assessment, and therefore, is not suitable for continuous and rapid monitoring, or for use in many settings (e.g., in a field hospital, at a sporting event, or in typical primary care settings). The following processing techniques can be used for raw data denoising to allow automatic denoising. Further, suitable methods for editing or denoising EEG or other signals are described in U.S. patent application Ser. No. 12/720,861, which is titled, "Method and Device for Removing EEG Arifacts," was filed on Mar. 10, 2010, and is incorporated by reference in its entirety. This is accomplished using standard signal processing components, which include digital filtering (low-pass filtering, bandpas filtering, etc.), thresholding, peak detection, and frequency-based processing.

There are seven typical types of noise that can contribute to poor signal quality. These include (1) horizontal/lateral eye movements (HEM), (2) vertical eye movements (e.g. blinks) (VEM), (3) cable or electrode movement causing over-range artifacts (PCM), (4) impulse artifacts (for example due to electrode "pops") (IMP), (5) electromyographic activity (also referred to as "muscle activity") (EMG), (6) significantly low amplitude signal (for example as a result of the suppression component of "burst suppression") (SLAS), and (7) atypical electrical activity pattern (for example due to paroxysmal brain activity) (AEAP). Out of these seven artifact types, two are non-physiological (type 3, type 4), three are physiological but are not brain-generated (type 1, 2, type 5) and two are brain-generated (type 6, type 7). All of these artifacts reflect a non-brain electrical activity, or abnormal brain-electrical activity. Further, in addition to recognizing artifacts of the types listed above, technologists typically remove short segments of the signal located (in time) immediately before and after the artifact. These segments are traditionally referred to as guardbands.

The automated denoising process described below includes artifact detector algorithms that can be used to independently identify the artifacts described above. These artifact detectors can work in parallel on a raw ABR data stream. In some embodiments, the duration of each artifact segment is computed to a resolution of 150 ms, each 15 ms segment referred to as a "sub-epoch". Each artifacting module produces a binary mask of size 1×10 indicating presence or absence of the artifact type in each of the sub-epochs.

The seven types of artifacts and the algorithms used for their detection are described below.

(1) Horizontal/Lateral Eye Movement (HEM/LEM):

To remove HEM artifacts, each electrode channel is band-pass filtered using an FIR filter with passband 0.5-3 Hz. The high-pass cut-off frequency of 0.5 Hz is chosen to ignore the influence of low-frequency activity occurring at frequencies below the delta_1 band (0.5-1.5 Hz). Candidate HEM sub-epochs are identified wherever the difference signal F7f-F8f exceeds a threshold of 24 μV. An additional measure, the mean-squared-error (mse) between −F7f and F8f is computed to help filter-out false detection of HEM. Cases where the mse is large (above a threshold) are indicative of an asymmetry between the two leads, which is likely to reflect presence of pathology rather than presence of HEM.

(2) Vertical Eye Movement (VEM)/Eye Opening/Eye Closing (EOEC):

Detection of vertical eye movement (VEM) (of which eye opening/closing is a sub-type) is performed by locating large "bumps" on leads Fp1 and Fp2, which are located right above the eyes. Since both eyes generally move in unison, the algorithm makes sure that only bumps that occur concurrently and in the same direction (same polarity) on Fp1 and Fp2 are identified as vertical eye movements. Each of the two signals, Fp1 and Fp2, is first low-pass filtered in the range 0.5-5 Hz.

Sub-epochs are then analyzed one at a time. In each sub-epoch, runs of samples exceeding a threshold of 24 μV are identified. In each such run, the global extremum is located and its value is compared to average signal values on either side of it. If $t_e$ denotes the time location of the extremum (in milliseconds), these average are taken over temporal windows $[t_e-320, t_e-100]$ and $[t_e+100, t_e+320]$. If the absolute difference between the extremum and either average exceeds the threshold, the sub-epoch is identified as a candidate VEM artifact. After this processing has occurred on both leads, the results are combined to turn candidate VEMs to true VEMs wherever they occurred concurrently on Fp1, Fp2 as described above.

(3) Patient Cable or Electrode Movement (PCM):

This is simply done by detecting excessively large signal magnitudes (also called "over-range") in any recorded channel. The default magnitude threshold is set to 120 μV. Generally, no guardband is implemented for artifacts of this type.

(4) Impulses (IMP):

To remove impulse artifacts, any recorded channel is first high-pass filtered with cutoff frequency at 15 Hz. This is done in order to remove the alpha component of cerebral electrical activity so that "sharp alpha" waves are not labeled as spikes. In each sub-epoch, the algorithm then looks at high-frequency activity. Successive windows of 100 ms width with 50% overlap are examined. Within each window, the value (max−min) is computed and compared to a threshold equal to 75 μV. Data greater than the 75 μV threshold is removed.

(5) Muscle Activity (EMG):

To remove EMG artifacts, any recorded channel is first band-pass filtered within the range 25-35 Hz (subband: β2) to produce a first signal (E2) and band-pass filtered in the range 15-25 Hz (subband: β1) to produce a second signal (E1). The variance (energy) of signal E1 on each lead, over the entire 2.5 second long epoch is computed. For each sub-epoch, the variance of signal E2 is also computed on each lead, and the relative energy of this signal with respect to the energy of signal E1 over the entire epoch is compared to a fixed threshold. The default threshold value is 155%. If, in at least one lead, the relative energy is larger than the threshold and the energy of E2 is larger than a minimum energy (currently set to 14 μV2), EMG detection is triggered.

(6) Significantly Low Amplitude Signal (SLAS):

This is meant to capture extremely low-amplitude EEG signals (at all frequencies), which occur, for example, when the brain is in burst suppression mode; a condition which can occur (but should be avoided) during anesthesia. No additional filtering of the EEG is used for detection of this activity. It can be detected by looking for signal epochs with mean-square energy below a threshold. Sub-epochs are examined four at a time, corresponding to a window size of 1 second. The overlap between consecutive groups of sub-epochs is 75%. The maximum signal energy (across leads) is computed and compared to a fixed threshold. The default threshold value is 12 μV2.

(7) Atypical Electrical Activity Pattern (AEAP):

This artifact type is meant to detect unusual patterns of activity in the EEG such as those which occur in the EEG of epileptic subjects during a convulsive or non-convulsive seizure. The algorithm is sensitivite to Spike-Wave complexes occurring in bursts over several hundred milliseconds. In this method raw EEG data is cleaned, and linear and non-linear averaging of that pre-cleaned data is performed. Then the linear and non-linear features of the single final averaged waveform is used to detect peak location and amplitude (using direct methods of peak detection and classification based on features, and to compare the features of the present averaged waveform to the features of pre-stored waveforms already correlated to ICP levels or other abnormalities.

Other embodiments will be apparent to those skilled in the art from consideration of the specification and practice of the devices and methods disclosed herein. It is intended that the specification and examples be considered as exemplary only, with a true scope being indicated by the following claims. A number of patents, patent publication, and nonpatent literature documents have been cited herein. Each of these documents is herein incorporated by reference.

What is claimed is:

1. A system for monitoring brain electrical activity of a patient, comprising:
   a set of electrodes;
   at least one auditory stimulus generator;
   a detection system operatively connected to the set of electrodes and configured to receive electrical signals detected by the electrodes after production of an auditory stimulus by the stimulus generator, the electrical signals representing the patient's auditory evoked response, and to transmit the electrical signals to a signal processor; and
   the signal processor configured to:
      reject artifacts present in the electrical signals using a plurality of automated artifact detectors working in parallel to generate artifact-free signals;
      perform non-linear denoising on the artifact-free signals to produce denoised signals;
      transform the denoised signals to a non-linear wavelet transform domain;
      automatically detect locations of one or more peaks of the patient's auditory evoked response in the non-linear wavelet transform domain;
      extract a set of quantitative non-linear features related to the patient's auditory evoked response; and
      compare the set of non-linear features to one or more feature sets stored in a storage system and determine if the non-linear features are indicative of an abnormal neurologic state.

2. The system of claim 1, wherein the processor is further configured to extract a set of linear features related to the patient's auditory evoked response.

3. The system of claim 1, wherein the storage system includes a database of normal values for auditory evoked response data.

4. The system of claim 1, wherein the storage system includes a database of auditory evoked response data for a group of patients, and the processor is configured to compare the set of non-linear features to one or more feature sets of the group of patients and to classify the patient's neurologic state based on the comparison.

5. The system of claim 4, wherein the patient's neurologic state is classified based on a similarity between one or more non-linear features of the patient's auditory evoked response and one or more non-linear features of at least one other patient having a known neurologic state.

6. The system of claim 1, wherein the storage system includes a database of prior auditory evoked response measurements from the same patient, and the signal processor is configured to compare the set of non-linear features to one or more feature sets stored from the prior measurements and determine if any changes have occurred.

7. The system of claim 1, wherein the signal processor is further configured to detect the amplitude or the timing of the one or more peaks in the patient's auditory evoked response.

8. The system of claim 1, further including a communication device configured to automatically generate a signal representing the patients neurologic state.

9. The system of claim 8, wherein the communication system includes a visual display indicating a deviation from a baseline measurement.

10. The system of claim 8, wherein the communication system includes a visual display indicating a deviation from a baseline measurement indicative of intracranial pressure for a patient.

11. The system of claim 1, wherein the electrode set is positioned on a head band and includes at least two electrodes positioned on the head band to allow detection of auditory evoked response signals when the headband is positioned on a patient.

12. The system of claim 1, further including a communication system configured to transmit data related to auditory evoked response signals to a location distant from the system.

13. The system of claim 1, wherein at least one of said automated artifact detectors is configured to detect at least one of: horizontal eye movements, vertical eye movements, impulse artifacts, muscle activity, or significantly low amplitude signal.

14. A method for monitoring brain electrical activity, comprising:
   providing an auditory stimulus to a patient, by a stimulus generator;
   obtaining electrical signals representing an auditory evoked response by using a set of electrodes located on the patient after production of the auditory stimulus;
   transmitting the electrical signals real-time to a signal processor;
   performing a real-time artifact rejection step on the electrical signals using a plurality of automated artifact detectors working in parallel to generate artifact-free signals;
   performing a non-linear denoising step on the artifact-free signals to produce denoised signals;
   transforming the denoised signals to a non-linear wavelet transform domain;
   automatically detecting locations of one or more peaks of the patient's auditory evoked response in the non-linear wavelet transform domain;
   extracting a set of quantitative non-linear features related to the patient's auditory evoked response; and
   comparing the set of non-linear features to one or more feature sets stored in a storage system and determining if the non-linear features are indicative of an abnormal neurologic state.

15. The method of claim 14, wherein comparing the set of non-linear features to one or more feature sets stored in a storage system includes comparing the features to a database of normal values for auditory evoked response data.

16. The method of claim 14, wherein comparing the set of non-linear features to one or more feature sets stored in a storage system includes comparing the features to a database of auditory evoked response data for a group of patients and classifying the patient's neurologic state based on the comparison.

17. The method of claim 16, wherein the patient's neurologic state is classified based on a similarity between one or more non-linear features of the patient's auditory evoked response and one or more non-linear features of at least one other patient having a known neurologic state.

18. The method of claim 14, wherein comparing the set of non-linear features to one or more feature sets stored in a storage system includes comparing the non-linear features to non-linear features from prior measurements of the same patient and determining if any changes have occurred for the same patient.

19. The method of claim 14, further comprising detecting the amplitude or the timing of the one or more peaks in the patient's auditory evoked response.

20. The method of claim 14, further including generating a signal representing the patient's neurologic state.

21. The method of claim 20, wherein the signal is a visual display.

22. The method of claim 20, wherein the visual display indicates a deviation from a baseline measurement indicative of intracranial pressure for the patient.

23. The method of claim 14, wherein the electrode set is positioned on a head band and includes at least two electrodes positioned on the head band to allow detection of auditory evoked response signals when the headband is positioned on the patient.

24. The method of claim 14, further including transmitting data related to repeated brain electrical activity measurements to a location distant from the system.

25. The method of claim 14, wherein at least one of said automated artifact detectors is configured to detect at least one of: horizontal eye movements, vertical eye movements, impulse artifacts, muscle activity, or significantly low amplitude signal.

26. The system of claim 13 or method of claim 25, wherein said horizontal eye movement artifacts detection comprises: band-pass filtering the electrical signals with an FIR filter, wherein the high-pass cut-off frequency of the band-pass filter is selected such that frequencies below the delta_1 band are removed; identifying one or more time segments of the electrical signals which correspond to a difference in electrical signals from an F7 electrode and F8 electrode exceeding a threshold as candidate segments having horizontal eye movement artifacts; and determining the mean-squared-error between the signals from the F7 electrode and F8 electrode to filter out false detection of horizontal eye movement artifacts if the mean-squared-error is above a threshold indicating presence of pathology rather than presence of horizontal eye movement artifacts.

27. The system of claim 13 or method of claim 25, wherein said vertical eye movement artifacts detection comprises: low-pass filtering portions of the electrical signals corresponding to an Fp1 electrode and an Fp2 electrode; identifying bumps in the low-pass filtered portions; determining whether a difference between a value of the global extremum of each bump and average values of the low-pass filtered portions of the electrical signal to the side of the bump exceed a threshold; and determining whether the bumps corresponding to Fp1 and Fp2 occur concurrently.

28. The system of claim 13 or method of claim 25, wherein said muscle activity artifacts detection comprises: band-pass filtering the electrical signals within a first range to produce a first band-passed signal and band-pass filtering the electrical signals within a second range to produce a second band-passed signal; determining a variance of the first band-passed signal over a first time-segment; determining a variance of the second band-passed signal over each of a plurality of a second time-segment that is a subsection of the first time-segment; and determining whether each of the variances for each second time-segment of the second band-passed signal relative to the variance of the first band-passed signal is above a threshold and whether the variance of each second time-segment of the second band-passed signal is above a minimum variance.

29. The system of claim 13 or method of claim 25, wherein said impulse artifacts detection, further comprises: high-pass filtering the electrical signals with a cutoff frequency to remove an alpha component of cerebral electrical activity; and identifying segments of the high-pass filtered electrical signals which include a difference between a maximum value and a minimum value that is greater than 75 $\mu V$.

30. The system of claim 13 or method of claim 25, wherein said significantly low amplitude signal detection comprises detecting segments of the electrical signals with a maximum mean-square energy acro one or more electrodes lower than a threshold of 12 $\mu V^2$.

* * * * *